United States Patent
Grünau

(10) Patent No.: US 7,263,172 B2
(45) Date of Patent: Aug. 28, 2007

(54) X-RAY APPARATUS HAVING MEANS FOR DETERMINING MOVABLE COMPONENT POSITIONS

(75) Inventor: Dieter Grünau, Hamburg (DE)

(73) Assignee: Koninklijke Philips Electronics, N.V., Eindhoven (NL)

( * ) Notice: Subject to any disclaimer, the term of this patent is extended or adjusted under 35 U.S.C. 154(b) by 119 days.

(21) Appl. No.: 10/520,308

(22) PCT Filed: Jul. 1, 2003

(86) PCT No.: PCT/IB03/03039

§ 371 (c)(1),
(2), (4) Date: Jan. 5, 2005

(87) PCT Pub. No.: WO2004/008077

PCT Pub. Date: Jan. 22, 2004

(65) Prior Publication Data

US 2005/0264434 A1    Dec. 1, 2005

(30) Foreign Application Priority Data

Jul. 10, 2002 (DE) .............. 102 30 972

(51) Int. Cl.
*H05G 1/28*     (2006.01)
(52) U.S. Cl. ............... 378/163; 378/195; 378/196; 378/197; 378/198; 356/614; 356/615; 356/617; 341/13
(58) Field of Classification Search ........ 378/179, 378/196–198; 341/13
See application file for complete search history.

(56) References Cited

U.S. PATENT DOCUMENTS

| | | | | | |
|---|---|---|---|---|---|
| 3,841,462 | A | * | 10/1974 | Schmidt | 198/345.1 |
| 4,097,746 | A | * | 6/1978 | Ingham et al. | 378/20 |
| 4,334,155 | A | * | 6/1982 | Gieschen et al. | 378/196 |
| 4,727,787 | A | * | 3/1988 | Schlosser | 83/522.21 |
| 4,916,725 | A | * | 4/1990 | Quinter et al. | 378/177 |
| 5,023,899 | A | * | 6/1991 | Ohlson | 378/196 |
| 5,048,070 | A | * | 9/1991 | Maehama et al. | 378/197 |
| 6,237,707 | B1 | | 5/2001 | Lyke et al. | |
| 6,634,790 | B1 | * | 10/2003 | Salter, Jr. | 378/209 |

FOREIGN PATENT DOCUMENTS

| | | |
|---|---|---|
| DE | 2831058 | 1/1980 |
| EP | 0381894 | 8/1990 |
| EP | 0541885 A2 | 5/1993 |
| EP | 1103791 | 5/2001 |

\* cited by examiner

*Primary Examiner*—Khai M. Nguyen

(57) ABSTRACT

The invention relates to an apparatus, notably an X-ray apparatus, which comprises two components which are displaceable relative to one another. A position visualization unit is arranged on one component of the apparatus and the other component of the apparatus is provided with an image acquisition unit whose acquisition zone contains a segment of the position visualization unit which changes due to the motion. The image acquisition unit acquires images of the segment present in the acquisition zone and applies such images to an evaluation unit which extracts position information from the images.

11 Claims, 4 Drawing Sheets

X-RAY APPARATUS HAVING MEANS FOR DETERMINING MOVABLE COMPONENT POSITIONS

This is a continous application of a 371 of PCT/I803/ 03039 filed on Jul. 01, 2003 which claims priority from German Application 10230972.8 filed on jul. 10, 2002.

The document DE2831058 describes an X-ray examination apparatus in which a movably arranged component of the apparatus is connected, via a rope, to a potentiometer which is provided on another component of the apparatus. When the component of the apparatus is moved, the potentiometer is adjusted in conformity with the motion, so that the position of the component of the apparatus can be determined on the basis of the electrical signals present across the potentiometer. However, because of the very intricate construction of the potentiometer, a system of this kind is very expensive. Moreover, the individual components are subject to a given degree of wear due to the mechanical adjustment of the potentiometer.

It is an object of the present invention to provide an apparatus, notably an X-ray apparatus, which comprises improved means for determining the position of components of the apparatus.

This object is achieved by means of an apparatus which comprises two components which are displaceable relative to one another, a position visualization unit which is provided on one component of the apparatus, or on a part which is connected thereto, an image acquisition unit which is provided on the other component of the apparatus, or on a part which is connected thereto, in order to acquire images of a segment of the position visualization unit which changes due to a relative motion between the components of the apparatus, and an evaluation unit for extracting position information from the images.

One component of the apparatus is provided with a position visualization unit whereby the position of this component of the apparatus can be determined relative to the other component of the apparatus.

Alternatively, the position visualization unit may also be arranged on a part which is connected to the relevant component of the apparatus, for example, on a part which is situated in the vicinity of the apparatus. There are many possibilities for mounting the position visualization unit. The position visualization unit may be mounted on the component of the apparatus as an independent unit, for example, by screwing or gluing. One possible alternative is to provide the position visualization unit directly on the surface of the component of the apparatus by printing or painting or by stamping or etching it into the material of the component of the apparatus. When a component of the apparatus is manufactured by molding or similar processes, the position visualization unit may also be formed in the component of the apparatus by suitably configuring the relevant mold.

Because of its configuration, for example, in respect of shape and color, a position visualization unit enables information as regards positions to be defined. The following are a few examples:

A position visualization unit consists of a plurality of position marks which define absolute position information (for example, numbers, words or another graphic symbol such as a triangle or a box) or relative position information with respect to other position marks (for example, strokes, dots or notches).

A position visualization unit may be, for example, a geometrical figure which is shaped such that for each visualized segment of the figure unambiguous information is offered as regards a position (for example, an elongate wedge which unambiguously identifies, on the basis of its width in a given position, the position of this location).

Furthermore, on the other component of the apparatus there is mounted an image acquisition unit in such a manner that the position visualization unit can move through the acquisition zone of the image acquisition device during a relative motion of the two components of the apparatus. When the image acquisition unit acquires an image, the part of the position visualization unit which is present in the acquisition zone at the instant of acquisition will be represented in said image. This image is applied to an evaluation unit which recognizes the shape of the segment of the position visualization unit represented therein so that it extracts the position information contained therein. This is possible, for example, by means of object recognition or text recognition methods which are known from the field of image processing. Because methods of this kind are widely known and used, they will not be further elaborated herein. The position of the two components of the apparatus can then be determined from the position information thus extracted.

The position visualization unit preferably extends substantially parallel to the path traveled during the motion. In the case of rectilinear motions, for example, the position visualization unit is arranged along a straight line which moves through the acquisition zone of the image acquisition unit during the motion.

The configuration of the position visualization unit is dependent mainly on the precision required for the determination of the position as well as on the degree of recognizability by the image acquisition unit and by the evaluation unit. Therefore, extremely economical position visualization units can be used in many cases. For example, preformed components such as measuring tapes can be used as a position visualization unit, or the position visualization unit can be designed by means of a graphical computer and a print can be provided on the relevant component of the apparatus. The construction of the image acquisition unit is also dependent on the required precision and can very often be economically realized by means of commercially available apparatus, for example, devices from the field of consumer products.

The means for position determination in accordance with the invention operate in a contactless manner, so that the maintenance work due to wear and the regular replacement of mechanical components are dispensed with.

There also are some further advantages: Nowadays computers are integrated in many X-ray apparatus. When this computer is additionally used as the evaluation unit, components can be saved and optimum use be made of the available resources.

In the previously mentioned position determination systems comprising rope-operated potentiometers a problem is encountered in the case of long, horizontally extending ropes, as slack of the rope gives rise to undesirable inaccuracies. The construction in the apparatus in accordance with the invention, however, is independent of the location of building in.

The position determination system is independent of the type of path (straight, curved, . . . ) along which the position visualization unit is moved relative to the image acquisition unit. The sole condition is that a segment of the position visualization unit must be present in the acquisition zone of the image acquisition unit.

When the position visualization unit is provided with a number of position marks, several of such position marks may be present in the segment of the position visualization unit which is present in the acquisition zone and hence in the images. The evaluation unit must then decide which of the position marks is the one describing the correct position. This is particularly simple when additionally at least one reference mark is reproduced in the image, the position of said reference mark being the same in each image. This can be realized, for example, in that for each image the evaluation unit utilizes fixed image points, such as a straight line through the image center, as a reference mark. Another possibility consists in making the image acquisition unit insert a reference mark in the images, so that a reference mark in the images is presented to the evaluation unit. A reference mark can be formed in the images in a particularly simple manner in conformity with claim 2. Should the position of the image acquisition unit change slightly during operation of the apparatus due to mechanical effects such as shocks, in all cases exact position determination is still possible for as long as a segment of the position visualization unit as well as the reference mark are reproduced in the images.

The implementation of the position visualization unit in conformity with claim 3 is particularly simple and economical. Commercially available measuring tapes can be used in conformity with the relevant construction.

When the components of the apparatus are one-dimensionally movable relative to one another, it makes sense to use an arrangement of the position visualization unit as disclosed in claim 4. In response to a motion of the component of the apparatus the position visualization unit is moved along a line through the acquisition zone of the image acquisition unit. If the component of the apparatus is journaled so as to be rotatable, the embodiment in conformity with claim 5 offers the possibility of simple implementation. The position visualization unit need not be provided completely on the one component of the apparatus.

If the one component of the apparatus cannot be provided with the complete position visualization unit for lack of space, it is advantageous to utilize an embodiment as disclosed in claim 6. The position visualization unit is then constructed as a self-contained component whereto the motion is transferred. The tape-like carrier may be constructed, for example, as an endless loop which is tensioned between two rollers and is connected to the one component of the apparatus in one location. The embodiment in conformity with claim 7 has a particularly large space-saving effect. The roller may be, for example, spring loaded by mounting a helical spring in the roller. As a result, the tape-like carrier remains tensioned at all times and is wound onto the roller in one of the directions of motion. When the direction of motion is reversed, the tape-like carrier will be unwound from the roller.

As for every image acquisition by means of an image acquisition unit, the object to be imaged, in this case being the segment of the position indication unit, must either reflect light or other electromagnetic radiation or emit it itself. If the position visualization unit is not constructed so as to be light emissive, the image acquisition can be rendered so as to be independent from ambient light in conformity with claim 8.

In order to enable an economical implementation of the apparatus, an embodiment in conformity with claim 9 is proposed. Depending on the desired accuracy, very economical CCD cameras from the field of home computers can be used for the image transmission via the Internet, that is, so-called WEB cams.

The apparatus in accordance with the invention can be used in many fields, for example, for machines or tooling equipment. A particularly advantageous application is a medical apparatus, in particular an X-ray apparatus as disclosed in claim 10. A contemporary X-ray apparatus comprises a plurality of mechanical components which are often arranged so as to be movable relative to one another and for which an instantaneous position of the relevant components relative to one another is of interest. For example, the X-ray source in such an apparatus may be arranged so as to be displaceable in three dimensions and also by rotation, or the height of the X-ray detector is adjustable. Means for positioning the object to be examined during the acquisition of the X-ray images, for example, a table, may also be three-dimensionally adjustable.

However, in conformity with claim 11 it is of particular interest to mention a ceiling stand (three-dimensional displacement device) which is mounted on the ceiling of an examination room and enables displacement of a mount for an X-ray source. In addition the mount can also be pivoted about an axis. These components of the X-ray apparatus for the positioning of the X-ray source already include four displaceable components whose position should be determined relative to one another.

The invention will be described in detail hereinafter with reference to the FIGS. 1 to 4. Therein:

Figure 1:
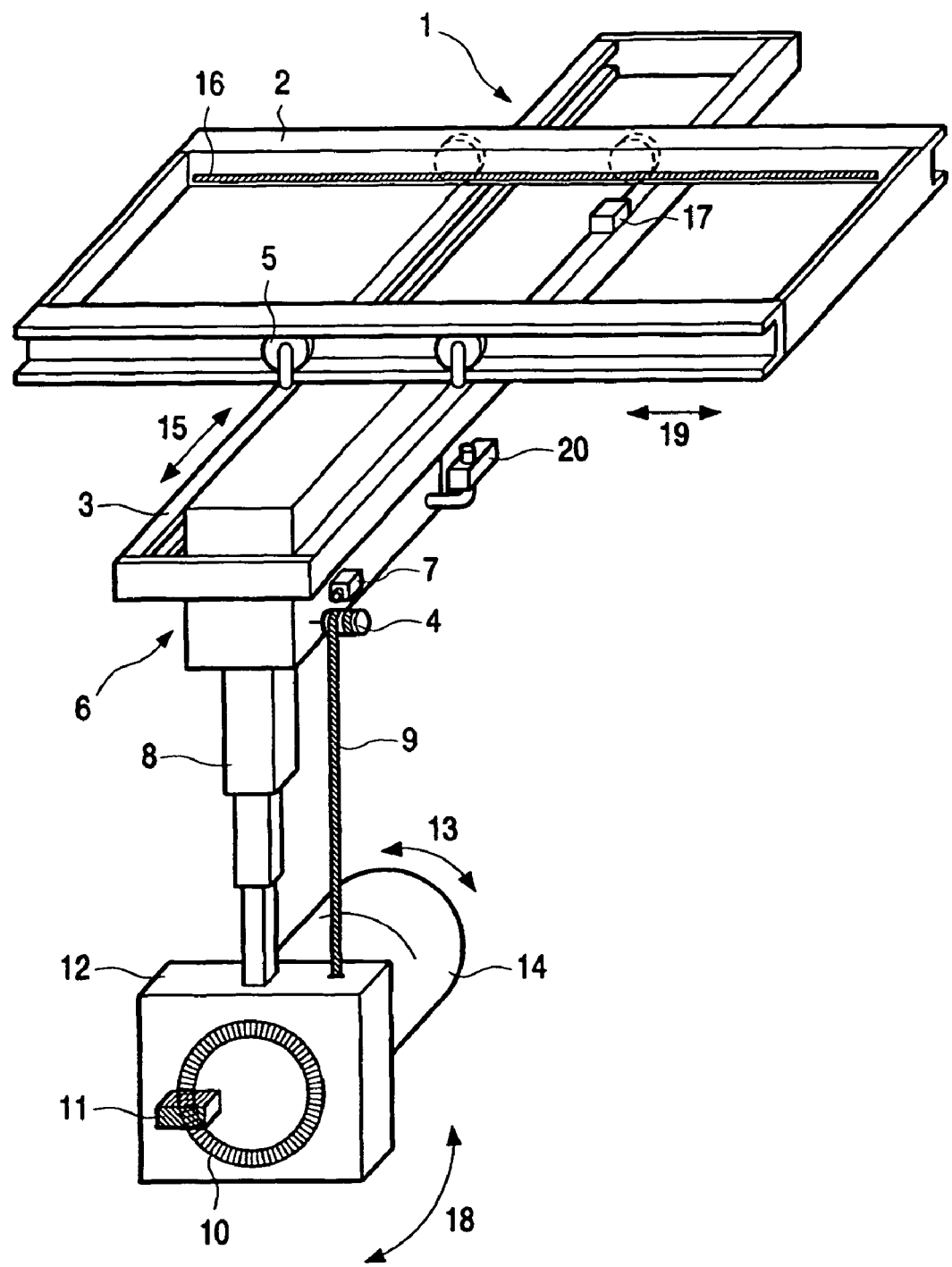
FIG. 1 shows a part of an X-ray apparatus.

FIG. 1 shows a part of an X-ray apparatus. The ceiling-mounted stand 1 serves to displace an X-ray source 14 in the three spatial directions. The mount 12 of the X-ray source 14 is attached to a telescope-like, vertical displacement device 8 which is connected to a horizontal displacement device via a carriage 6. To this end, the carriage 6 is arranged so as to be displaceable in the direction 15, via a roller system (not shown), on a first rail system 3 and the first rail system 3 is arranged so as to be displaceable on a second rail system 2 via rollers 5 in the direction 19. The second rail system 2 is mounted, for example, on the ceiling of an examination room.

On the second rail system 2 there is mounted a position visualization unit 16 wherefrom images can be acquired by means of a camera 17. When the first rail system 3 moves in the direction 19, the position visualization unit 16 moves past the camera 17. The images acquired by the camera 17 show a segment of the position visualization unit 16 which corresponds to the position of the rail system 2 relative to the camera 17 (or relative to the rail system 3), so that the relevant position can be determined from the images. Alternatively, the position visualization unit could also be mounted on the ceiling so as to extend parallel to the displacement direction 19; in that case the camera 17 should be oriented accordingly.

Figure 2:
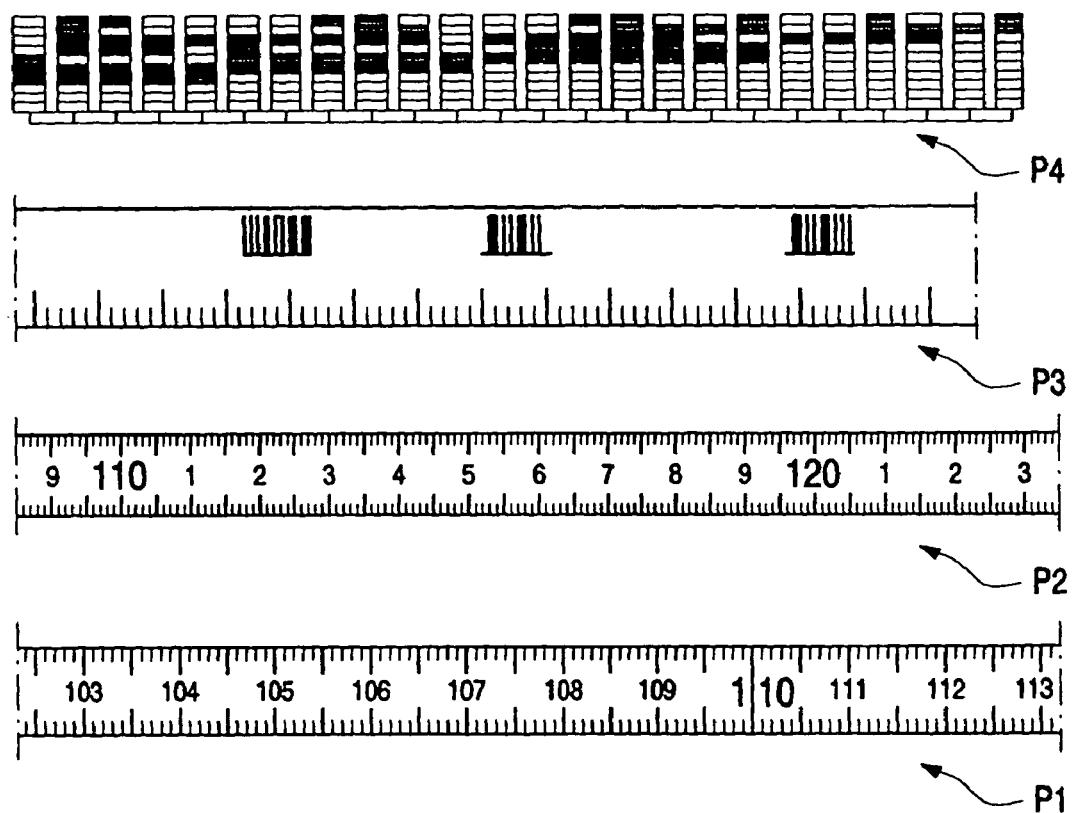
FIG. 2 shows position visualization units in the form of different measuring tapes.

FIG. 2 shows three examples of a position visualization unit which is suitable for use as the position visualization unit 16 in FIG. 1. The position visualization units are shaped as a tape and consist of position marks which are configured and arranged in conformity with a scale which is similar to that provided on commercially available measuring tapes or folding rules. The position visualization unit P1 comprises consecutively numbered units of length which are counted from "103" to "113" in the segment shown. In addition to the number, a long stroke is provided for each unit of length. Each unit of length is subdivided into ten sub-units which are represented by a respective short stroke. The stroke halfway the unit of length is slightly longer than a short stroke. The unit of length shown is dependent on the accuracy required in the system and may be, for example, a millimeter, a centimeter or a decimeter. If the unit of length is a centimeter, the distance between two units of length amounts to 1 cm and the distance between two sub-units amounts to 1 mm. Using a position visualization unit of this kind, an accuracy of at least 1 mm can be achieved. The position visualization unit P2 is very similar to the position visualization unit P1. The counting of the units of length, however, is now different in that only the last digit of the relevant number is shown between blocks of ten.

In the position visualization unit P3 each unit of length is denoted by a long stroke and each sub-unit is denoted by a short stroke. However, the numbers no longer consist of digits but are represented in coded form by a bar code, thus simplifying the recognition in the image and also the evaluation of the units of length by the evaluation unit. For further simplification of the image evaluation in the evaluation unit, the position marks of the position visualization units may have not only a different shape but also a different color. The upper position visualization unit P4 constitutes an alternative representation of the numbers by way of a bar code, each sub-stroke now being the same and a bar code being provided over each sub-stroke.

Figure 3:
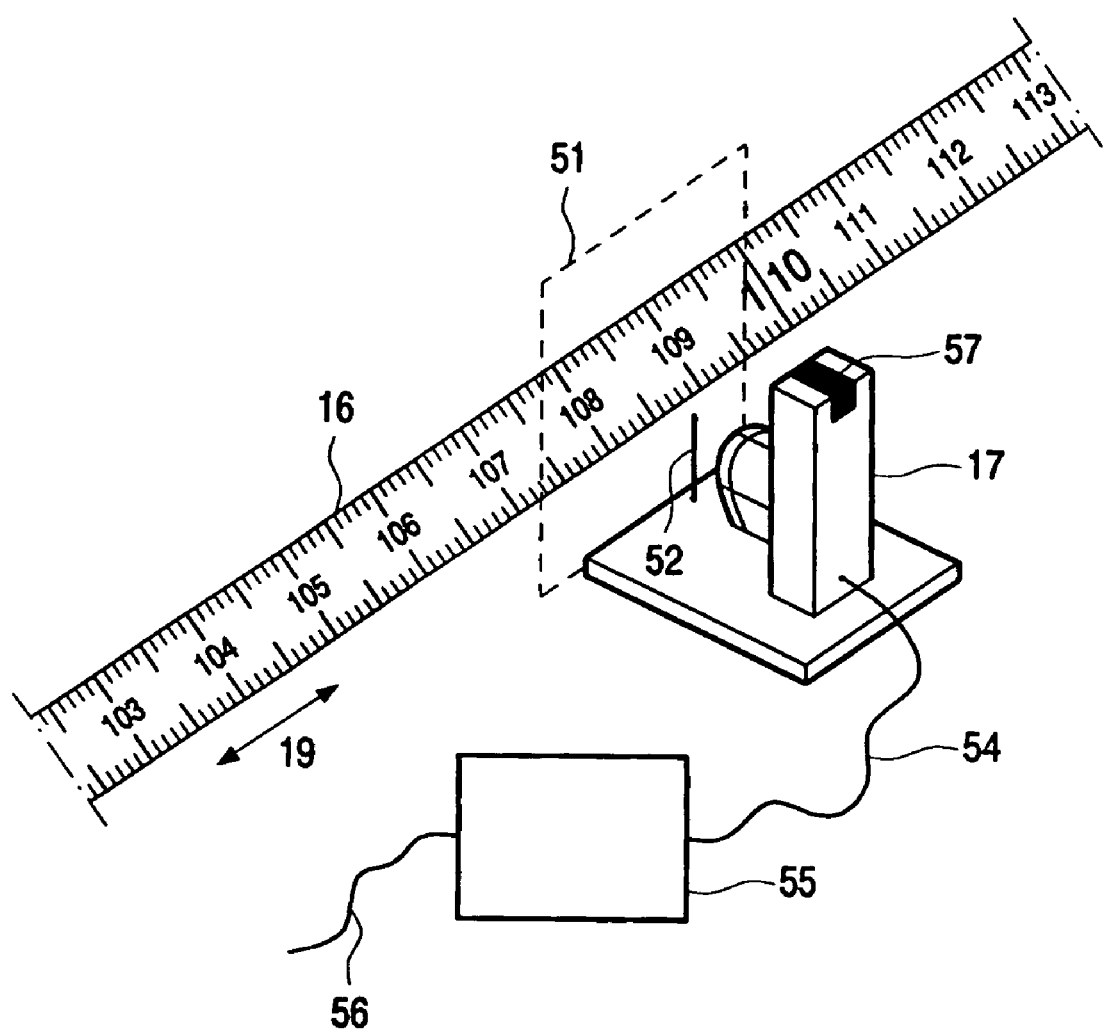
FIG. 3 shows the construction principle of an apparatus in accordance with the invention.

FIG. 3 is a more detailed representation of the co-operation between the position visualization unit 16 and the camera 17 as shown in FIG. 1. The camera 17, being directed towards the tape-like position visualization unit 16, acquires an image of a part of the position visualization unit 16, said image being represented by the acquisition zone 51 of the camera 17 which is enclosed by the dashed line. A pointer 52, being provided in the vicinity of the position visualization unit, is also present in the acquisition zone 51 as a reference mark. Alternatively, the pointer may also project into the position visualization unit or traverse the entire acquisition zone 51. Furthermore, the pointer 52 is linked to the camera 17, so that the pointer 52 is always positioned in the same position in the acquisition zone 51. The pointer 52 can be dispensed with if a corresponding reference mark, for example as already mentioned at the beginning of this document, is inserted in the image in a different way, for example, in that the camera 17 or the evaluation unit inserts a "virtual" reference mark in the images. Such a virtual reference mark could in this case be formed by a straight line which extends parallel to the pointer 52 or substantially parallel to the strokes of the position visualization unit 16, so approximately vertically through the images.

Furthermore, an illumination unit 57 is integrated in the camera 17, which illumination unit illuminates the zone of the pointer 52 and the position visualization unit 50 present each time in the acquisition zone. Alternatively, the illumination unit 57 may also be constructed as a self-contained component which is arranged, for example, adjacent the camera 17.

When the position visualization unit 16 moves through the acquisition zone 51 in the direction 19 (parallel to the direction of the tape), the tip of the pointer 52 points towards each time different position marks of the position visualization unit 16. The camera 17 acquires images of the segment of the position visualization unit 16 which is present in the acquisition zone 51 and applies these images, via a lead 54, to the evaluation unit 55. The evaluation unit 55 then extracts information as regards the segment of the position visualization unit 16 imaged in the examination zone 51 as well as regards which position marks of the position visualization unit 16 are present in the vicinity of the pointer 52. The data transmission between the camera 17 and the evaluation unit 15 can alternatively take place in a wireless manner. In the example shown in FIG. 3 the evaluation unit 55 recognizes that the pointer 52 is situated approximately at the ninth sub-stroke to the right of the stroke of the unit of length which bears the number 108. When the unit of length represents a centimeter, the pointer points to 108.9 cm. When the pointer 52 is present between two sub-strokes, the evaluation unit defines the position-determining mark as the sub-stroke whose distance from the pointer 52 is the smallest. The information thus extracted can be applied from the evaluation unit 55, by way of suitable data transmission means such as a lead 56 in the present case, to further components of a system.

In FIG. 1 a system of this kind, consisting of a position visualization unit and a camera, can also be found on the carriage 6 and on the first rail system 3. To this end, a camera 20 is mounted on the carriage 6 and a further tape-shaped position visualization unit (not visible in this case) is mounted on the lower side of the rail system 3 in such a manner that the camera 20 can acquire images thereof. When the carriage 6 moves in the direction 15, segments of the position visualization unit which correspond, in relation to the position of the carriage 6, to the first rail system 3 are present in the acquisition zone of the camera 20 and an evaluation unit (not shown in this case) can extract corresponding positions from the images.

Furthermore, a spring-loaded roller 4 is attached to the carriage 6, a tape 9 of a flexible material being wound onto said roller as a position visualization unit. The tape 9 is constructed, for example, as shown in FIG. 2 and can be unwound from the roller against the force of the spring. The outer end of the tape 9 is attached to the mount 12 of the X-ray source 14. When the mount 12 is moved downwards from an upper position by means of the vertical displacement device 8, the tape 9 is unwound from the roller 4. When the mount 12 is moved upwards again, the tape 9 is wound onto the roller 4 again by the force of the spring. In the vicinity of the roller 4 there is provided (again mounted on the carriage 6) a camera 7, a segment of the tape 9 being present in the acquisition zone thereof. This third system, consisting of the position visualization unit and the camera, enables the position of the mount 12 to be determined, and hence also the position of the X-ray source 14 relative to the carriage 6.

A further camera 11 is mounted on the mount 12. An annular position visualization unit 10 is mounted on the X-ray source 14 which is journaled so as to be rotatable in the mount 12, a segment of said position visualization unit being present in the acquisition zone of the camera 11. The segment of the position visualization zone 10 which is present in the acquisition zone is changed by rotation of the X-ray source in the direction 13. The rotary position of the X-ray source 14 relative to the mount 12 can be determined on the basis of the images acquired by the camera 11. A further system, formed by a position visualization unit and a camera (not shown in this case), can be mounted on the attachment of the vertical displacement device 8 to the mount 12 so as to derive the position during a rotation of the mount 12 around the vertical displacement device 8 in the direction 18.

All of the cameras shown in FIG. 1 can be coupled to a common evaluation unit which is accommodated, for example, in the carriage 6. The coupling may be either wireless or be realized via leads. Alternatively, the evaluation unit may also be arranged as an independent unit adjacent the system components shown, or be integrated in existing system components. Because a complex X-ray examination system generally comprises programmable data processing units, the evaluation unit can be comparatively simply integrated therein by extending the program code and slightly modifying the external connections. A further alternative is to accommodate the evaluation unit in a housing together with the camera, so that relevant position information can be derived directly from the combined camera/evaluation unit.

The position information determined by the evaluation unit can be used in various manners. For example, the positions of the relevant components of the apparatus can be displayed for a user on a monitor (not shown). The position information can also be used by an automatic displacement device. The movable components in FIG. 1 can then be displaced, that is, by way of motors, to selectable positions; a control unit then receives the respective instantaneous position of the relevant components of the apparatus from the evaluation unit during the displacement so that it can control the displacement.

Figure 4:
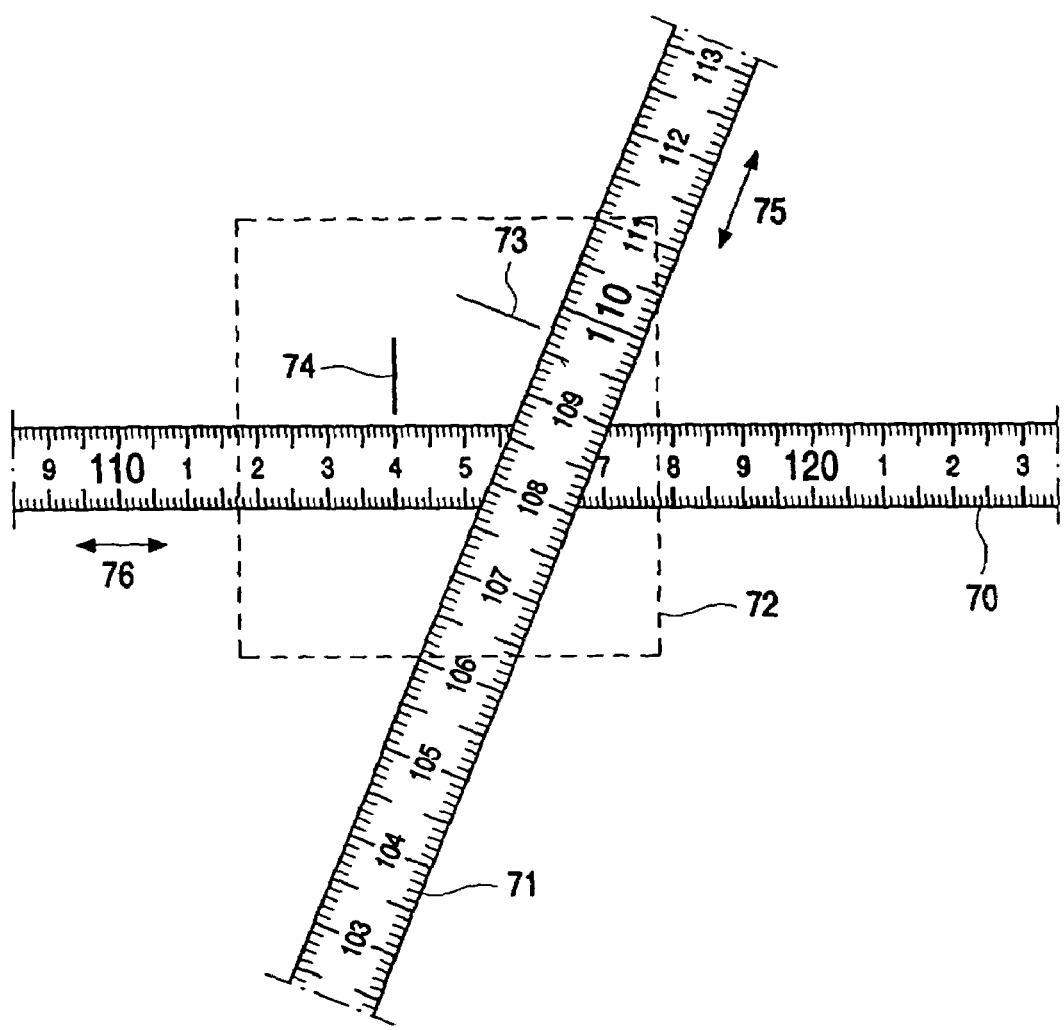
FIG. 4 shows a plurality of measuring tapes in an acquisition zone.

FIG. 4 shows a first tape-like position visualization unit 70 which is capable of movement in the direction 75 through the acquisition zone 72 of a camera (not shown), and also a second tape-like position visualization unit 71 which can move through the acquisition zone 72 in the direction 76. Also shown is a first pointer 74 which is associated with the position visualization unit 70, and a second pointer 73 which is associated with the position visualization unit 71. This arrangement enables the simultaneous acquisition of images of two position visualization units, moving through the acquisition zone 72 in different directions, by means of a single camera. Such an arrangement can be used, for example, in the system of FIG. 1 if the camera 20 is arranged on the carriage 6 in such a manner that its acquisition zone contains the tape 9 on the roller 4 as well as the position visualization unit (not visible in this case) mounted on the lower side of the first rail system 3. Virtual reference marks can again be used as an alternative for the pointers 73 and 74 in this case.

It is to be noted that FIG. 1 shows merely a part of an X-ray apparatus. Positions of displaceable components which are not shown in this Figure, for example, the position of an X-ray detector or of an examination table, can also be determined in accordance with the invention.

The invention claimed is:

1. An apparatus which comprises two components which are displaceable relative to one another, a position visualization unit which is provided on one component of the apparatus, or on a part which is connected thereto, an image acquisition unit which is provided on the other component of the apparatus, or to a part which is connected thereto, in order to acquire images of a segment of the position visualization unit which changes due to a relative motion between the components of the apparatus, and an evaluation unit for extracting position information from the images.

2. An apparatus as claimed in claim 1, comprising a reference mark which is visible in the images and is attached to the image acquisition unit.

3. An apparatus as claimed in claim 1, comprising a position visualization unit which is constructed in the form of a measuring tape.

4. An apparatus as claimed in claim 1, in which a relative motion occurs which extends along a substantially straight line, and which comprises a position visualization unit which is arranged parallel to said straight line.

5. An apparatus as claimed in claim 1, comprising a position visualization unit which is arranged along a circular line, one of the components of the apparatus being journaled so as to be rotatable.

6. An apparatus as claimed in claim 1, comprising a position visualization unit on a tape-like carrier.

7. An apparatus as claimed in claim 6, comprising a tape-like carrier which is connected on the one side to the one component of the apparatus and on the other side to a roller which is mounted on the other component of the apparatus, said carrier being wound onto or unwound from the roller as a result of the relative motion.

8. An apparatus as claimed in claim 1, comprising illumination means for illuminating the acquisition zone.

9. An apparatus as claimed in claim 1, comprising an image acquisition unit in the form of a charge-coupled device camera.

10. An X-ray apparatus which comprises two components which are displaceable relative to one another, a position visualization unit which is provided on one component of the apparatus, or on a part which is connected thereto, an image acquisition unit which is provided on the second component of the apparatus, or on a part which is connected thereto, in order to acquire images of a segment of the position visualization unit which changes due to the motion, and an evaluation unit for extracting position information from the images.

11. An X-ray apparatus as claimed in claim 10, characterized in that an X-ray source is arranged on the one component or the other component of the apparatus.

* * * * *